(12) United States Patent
Göbel

(10) Patent No.: US 7,794,425 B2
(45) Date of Patent: Sep. 14, 2010

(54) GASTRO-ESOPHAGEAL REFLUX CONTROL SYSTEM AND PUMP

(75) Inventor: Fred Göbel, Wilhelmsfeld (DE)

(73) Assignee: Kimberly-Clark Worldwide, Inc., Neenah, WI (US)

(*) Notice: Subject to any disclaimer, the term of this patent is extended or adjusted under 35 U.S.C. 154(b) by 435 days.

(21) Appl. No.: 11/643,441

(22) Filed: Dec. 21, 2006

(65) Prior Publication Data

US 2008/0154191 A1 Jun. 26, 2008

(51) Int. Cl.
*A61M 29/00* (2006.01)
(52) U.S. Cl. .................................. 604/101.05
(58) Field of Classification Search ............ 604/101.05
See application file for complete search history.

(56) References Cited

U.S. PATENT DOCUMENTS

| | | | |
|---|---|---|---|
| 4,174,637 A | 11/1979 | Mulzet et al. | |
| 4,666,433 A | 5/1987 | Parks | |
| 4,685,901 A | 8/1987 | Parks | |
| 4,701,163 A | 10/1987 | Parks | |
| 4,798,592 A | 1/1989 | Parks | |
| 4,845,487 A | 7/1989 | Frantz et al. | |
| 4,921,481 A | 5/1990 | Danis et al. | |
| 5,078,682 A | 1/1992 | Miki et al. | |
| 5,514,102 A | 5/1996 | Winterer et al. | |
| 5,718,685 A | 2/1998 | Roewer et al. | |
| 5,720,721 A | 2/1998 | Dumas et al. | |

(Continued)

FOREIGN PATENT DOCUMENTS

WO WO 92/17150 10/1992

(Continued)

*Primary Examiner*—Nicholas D Lucchesi
*Assistant Examiner*—Jason Flick
(74) *Attorney, Agent, or Firm*—Karl V. Sidor; Sue C. Watson; James B. Robinson

(57) ABSTRACT

An enteral feeding unit or system that minimizes the occurrence of gastro-esophogeal-pharynegal reflux during feeding is described. The enteral feeding unit or device includes an automatable feeding pump with a feedback sensor for sensing a relative pressure in a patient's stomach and esophagus, and a regulator system for controlling or monitoring feeding rate to said patient as a function of said relative gastro-esophageal pressure. The system includes a stomach probe that has a fluid-tight closure of the esophagus. The stomach probe, according to the invention, is characterized by a tampon-bladder for watertight closure of the esophagus, in which the tampon-bladder forms from flexible and/or elastic material at least a closed inner cavity for the reception of a fluid medium, through a means (11) of establishing a prescribed pressure for the medium in the tampon-bladder (16) by an inner lumen forming the actual stomach probe, from which an outer hose-like lumen (18) extending to the tampon-bladder (16) is so arranged that between the outer lumen (18) and the inner lumen (17) a channel is formed connected to the inner cavity of the tampon-bladder (16) arranged on the outer lumen (18) by a number of openings (20), whereby the inner cavity of the tampon-bladder (16) is connected via the canal formed between the inner and outer lumina (17, 18) with the means of production of pressure in the tampon-bladder, that is, with a suitably graded reservoir or equalizing vessel (11) for the liquid medium situated above the tampon-bladder and outside the patient.

3 Claims, 4 Drawing Sheets

U.S. PATENT DOCUMENTS

| | | |
|---|---|---|
| 5,951,510 A | 9/1999 | Barak |
| 6,213,972 B1 | 4/2001 | Butterfield et al. |
| 6,259,938 B1 | 7/2001 | Zarychta et al. |
| 6,334,064 B1 | 12/2001 | Fiddian-Green |
| 6,551,272 B2 | 4/2003 | Göbel |
| 2008/0167607 A1* | 7/2008 | Pfeiffer et al. ........... 604/97.01 |

FOREIGN PATENT DOCUMENTS

| | | |
|---|---|---|
| WO | WO 93/18324 | 9/1993 |
| WO | WO 2004/014455 | 2/2004 |

* cited by examiner

GASTRO-ESOPHAGEAL REFLUX CONTROL SYSTEM AND PUMP

FIELD OF INVENTION

The present invention relates to a system for preventing gastro-esophageal reflux by regulating or counterbalancing stomach pressure generated during gastric-enteral feeding of a patient. In particular, the invention involves forming a pressure-regulated seal against the gastro-esophageal sphincter by means of an inflatable tampon-bladder.

BACKGROUND

Enteral feeding is a form of hyperalimentation and metabolic support in which nutrient formulas or medicaments are delivered directly to the gastrointestinal tract, either the stomach or the duodenum. Nutrient administration is accomplished through use of an enteral feeding system or device. Certain enteral feeding devices include pumps which deliver feeding fluid to the patient. Other enteral feeding devices rely upon gravity to move the feeding fluid from a container (suspended above patient level) to the patient.

During enteral feeding, excessive gastric pressure may result from the accumulation of gas or liquid resulting from stomach contractions, movement of the patient's abdomen, crying or through normal formation of gas. From time to time, the body relieves such excess gastric pressure by expelling gas or liquid or reflux fluid. The term, "reflux fluid" as used herein includes any gas, any liquid, any partially solid and liquid substance or any material which the body can expel.

Typically the expulsion of reflux fluid occurs during a burping response in which reflux fluid is expelled upward from the stomach through the esophagus and is expressed out of the mouth, where the enteral feeding tube is orally intubated or through the nasal passages, where naso-pharyngeal intubation has been utilized. When the patient expels reflux fluid, the reflux fluid often flows out of the patient's mouth or the nose. The enteral feeding device is not adapted to receive the back flow of reflux fluid. Specifically, the feeding fluid pressure in the enteral feeding device prevents reflux fluid from flowing from the patient into the patient feeding tube.

Though gastric reflux pressure created by even limited episodes of stomach movement or crying may exceed several feet of water, such reflux pressure can be inadequate to overcome the greater forward fluid pressure present within the patient feeding tube. As a result, expelled reflux fluid can be trapped or accumulate in or around the nasal, oral, or pharyngeal passages, which often can lead to complications. This accumulation of reflux fluid is undesirable because the patient loses feeding fluid, and moreover, it is possible for the patient to inhale the reflux fluid into the lungs with possible risk of aspiration pneumonia, bacterial infection in the pharynx or esophagus, or other ailments. The problem of gastric reflux pressure and reflux fluid is most acute in neonates, infants and small children in which gastric pressure may rapidly accumulate through periodic episodes of crying and because such patients have yet to develop control over the burping response as a means of gastric pressure relief. However, it is not unusual for adult patients undergoing enteral feeding to experience occasional difficulties with gastric reflux pressure relief.

Over the years, enteral tubes for providing food and medication to a patient have been used in medical settings for many years. For examples of enteral feeding devices are described in U.S. Pat. Nos. 4,666,433, 4,701,163, 4,798,592, or 4,685,901. The measurement of esophageal and gastric pressures with balloon-tipped catheters also has been employed with great success over the past half century to delineate the physiology of the respiratory system. Gastro-esophageal reflux (GER) and bronchoaspiration of gastric content are risk factors linked with ventilator-associated pneumonia. Gastroesophageal reflux (GER) occurs in critically ill patients even in the absence of nasogastric (NG) tubes and enteral feedings; up to 30% of patients who are kept in the supine position are estimated to have GER. At least two studies have shown a reduction of GER when critically ill patients are kept in the semirecumbent position. The upper gastrointestinal tract of a critically ill patient receiving enteral feedings is additionally challenged by (1) gastrointestinal intubation, (2) rate of feeding, and (3) type of enteral formula.

The lower esophageal sphincter (LES) has been recognized for more than three decades as the primary physiologic factor preventing GER. A number of studies in adults and children with or without reflux disease have examined the relationship of LES pressure to occurrence and time of reflux, using concurrent measurements of esophageal motility and pH. One consistent finding has been that under resting conditions, LES pressure has to be absent for reflux to occur. The NG tube may predispose a patient to reflux by interfering with LES function, as well as prolonging esophageal contact time with refluxed gastric contents.

The majority of enteral feeding tubes remain in the stomach. Regurgitation occurs even in patients with well-placed NG tubes and less frequently in patients with nasoduodenal (ND) or nasojejunal (NJ) tubes. Several studies have shown that NG tubes may increase the prevalence of GER in supine patients from 15% to 80% of cases. Placement of an NG tube may be associated with profound esophagitis within a 24-36-hour period, although it is more commonly observed after a week or more of intubation.

Fluids that commonly accumulate in the gastrointestinal tract of a tube-fed patient include the tube-feeding formula, swallowed saliva (>0.8 L/day), gastric secretion (1.5 L/day), and regurgitated small bowel secretion (2.7-3.7 L/day) into the stomach. When gastrointestinal motility is normal, secretions and ingested fluids are propelled forward and absorbed with little difficulty. Significant gastrointestinal dysmotility, ranging from moderate delay in gastric emptying to marked gastric paresis, has been described in patients with a variety of clinical conditions such as burns, sepsis, trauma, surgery, and shock.

SUMMARY OF THE INVENTION

The invention rectifies the disadvantages associated with conventional stomach probes and enteral feeding tubes. The present invention discloses a stomach probe that enables a clinician to close off or fill of a patient's esophagus, but without deleterious effect on its wall structures.

In one aspect the invention relates to an enteral-feeding control device that includes: an automatable feeding pump with a feedback sensor for sensing a relative pressure in a patient's stomach and esophagus, and a regulator system for controlling or monitoring feeding rate to said patient as a function of said relative gastro-esophageal pressure.

As an alternative characterization, the present invention describes an anti-gastro-esophageal reflux device for use during enteral feeding. The device includes: a tube having a double lumen, a gastric bladder, and esophageal bladder connected by a conduit to a pressure-regulating unit, said esophageal bladder having a compressible volume and an outer surface with an plurality of pleats that can intermesh with a patient's esophagus wall structures, and said pressure-regulating unit maintains a pressure within said esophageal bladder at a level greater than gastric pressure exerted on said gastric bladder.

In another characterization, the invention pertains to an apparatus for controlling gastro-pharyngeal reflux in a patient. The apparatus includes: an enteral feeding tube having a double lumen, a gastric balloon, an esophageal balloon, a sensor for monitoring gastric pressure when enteral feeding is in process, and a external pump that regulates air or fluid pressure within said esophageal balloon, said sensor receives a signal that is averaged using a filter algorithm that sets a gradient value that is added to actual gastric pressure, thereby defining a relative level of esophageal pressure applied to seal from gastro-pharyngeal reflux. The esophageal balloon is inflatable with either a liquid or a gaseous fluid. The apparatus may further include a feeding pump that senses and adjusts relative amount of pressure in a patient's stomach as well as esophagus.

In another aspect the present invention relates to a process for effectively reducing gastric reflux into a patient's esophagus. The process or method involves: providing an enteral feeding tube having a double lumen, a gastric balloon, and an esophageal balloon; inserting said enteral feeding tube into said patient's upper alimentary canal, to position said gastric balloon in said patient's stomach and said esophageal balloon in said patient's esophagus; providing an sensor for monitoring gastric pressure when enteral feeding is in process; receiving a signal that is averaged using a filter algorithm; setting a gradient value that is added to actual gastric pressure, thereby defining a relative level of esophageal pressure applied to seal from gastro-pharyngeal reflux.

Other features and advantages of the present system and individual devices or components will become evident from the following detailed description. It is understood that both the foregoing general description and the following detailed description and examples are merely representative of the invention, and are intended to provide an overview for understanding the invention as claimed.

DETAILED DESCRIPTION OF THE INVENTION

Figure 1:
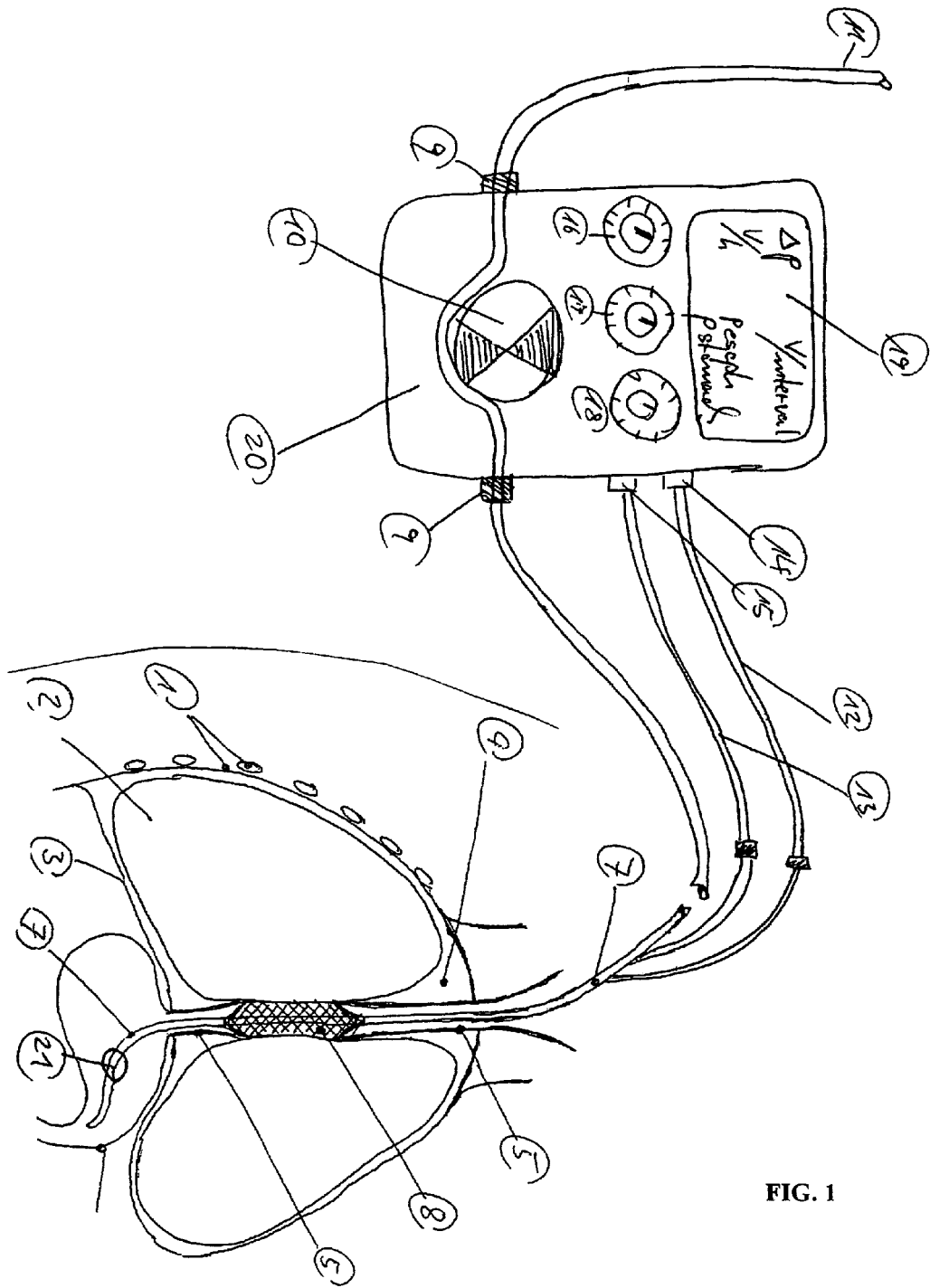
FIG. 1 is a general schematic representation of the present invention as inserted in a silhouette outline of a patient's head, torso and upper abdomen with a diagram of a pump system according to the present invention.

Pharyngeal reflux of gastric enteral feeding tubes in intubated patients, both ventilated and spontaneously breathing, is a common problem. Designed to prevent gastric content refluxing into a patient's pharynx esophagus, the esophageal balloon of the present invention extends to fill the entire esophagus passage way. The balloon when fully inflated has a larger volume that the distended esophagus; hence, the balloon has a number of interpleatings along its surface adapted to engage with the ridges and pleated lining of the esophagus. The present invention can prevent migration of feeding into the pharyngeal and paranasal cavities, from where it is difficult to remove and can become a breeding ground for VAP pathogenic bacteria.

During peristalsis, the lower esophageal sphincter (LES), where the esophagus meets the stomach, allows the food bolus to pass into the stomach. It prevents chyme (a mixture of bolus, stomach acid and digestive enzymes) from returning up the esophagus. The LES is aided in the task of keeping the flow of materials in one direction by the diaphragm. Deficiencies in the strength or the efficiency of the LES lead to various medical problems.

Material rising up into the pharynx from the stomach and intestinal tract represents, particularly for the unconscious patient being ventilated, a permanent reservoir of microbes, and may provoke or exacerbate pulmonary infection from the lower pharynx on intubation. Artificially ventilated intensive care patients are looked after through secretion-stimulating gastric probes or feeding tubes whose throughput as a rule is still insufficient to put a stop to gastro-esophageal-pharyngeal reflux beside or along them. As a result, many sedated or artificially ventilated patients are virtually overwhelmed by high-grade bacterially contaminated material in the pharyngeal, nasal and postnasal regions.

The present invention involves a pressure regulating device and/or system for use in facilitating enteral feeding of patients that require either short-term or long-term care. The pressure regulating device includes a mechanical pump, an esophageal bladder or balloon, and a gastric bladder or balloon. The pump can be composed of two sections. One section provides automated monitoring of the relative gastric and thoracic pressures and control over the inflation of the esophageal balloon so as to ensure a tight seal against the lower esophageal sphincter under feeding conditions. The other, second section controls the relative feeding rate to a patient as a function of the gastric pressure sensed through the gastric balloon. The present enteral feeding device can continuously monitor the intra-gastric pressure to determine the relative for slope of the pressure gradient applied to inflate or deflate the esophageal bladder.

A regulator unit can provide automated regulation of patient feeding rates, and can actively keep the seal pressure of the esophageal balloon in dynamic accordance with the actual intra-gastric pressure, in a fashion that a seal-sufficient pressure gradient between intra-esophageal pressure can be continuously maintained.

The present invention includes a gastric probe for introduction into the esophagus of the patient. The gastric probe has an inflatable esophageal bladder or balloon that can be subjected to a fill pressure of less than about 25 mbar, not to exceed about 60 mbar over short periods of about 2-3 hours. The pressure within the esophageal bladder prevailing can be ascertained continuously or intermittently; the fluctuations in the intra-thoracic pressure that are transmitted to the balloon of the gastric probe are detected and evaluated and supplied to the ventilator for controlling the breathing gas flow. By inflation of the esophageal bladder, the gastric probe that can be introduced into the esophagus is placed against the wall surface of the esophagus, which in its middle and (even better) lower third transmits the pressure course inside the thorax through the wall of the esophagus (transmurally) to the esophageally placed balloon of the gastric probe. The transmurally transmitted pressure is picked up by this balloon and made usable as a measured value and control signal.

In the method of the invention, the pressure in the esophageal bladder of the gastric probe is measured by a measuring instrument, and the measured values are transmitted by means of a measuring line that extends from the bladder to a ventilator or to a control device for the ventilator. The values obtained by measuring the esophageal bladder pressure are used to characterize the respiratory work done by the patient, and from pressure-supported respiratory cycles of fixed duration, cyclical respiratory work graphs are ascertained and made visible on a monitor in the form of pressure-volume loops.

The intra-cuff pressure of the tube is also measured by means of a measuring instrument, and the measured values are transmitted by means of a measuring line extending from the cuff of the tube to the ventilator, or to a control device for the pump. In order to detect the esophageal pressure, equivalent to an intra-thoracic pressure, the system for assisted or controlled inflation of the balloon cuff with an air or fluid source is outfitted with a gastric probe equipped with an inflatable balloon of a microthin-walled elastic plastic film with a wall thickness of less than or equal to about 0.03 mm, and the gastric probe balloon is subjected to a fill pressure of less than or equal to 25 mbar; a measuring instrument for detecting the esophageal bladder pressure prevailing in the gastric probe balloon is also provided, and the values for the esophageal balloon pressure, detected continuously or intermittently by the measuring instrument, can be delivered to the control device of the ventilator via a measuring line. To set a desired fill pressure in the gastric probe balloon, a measuring and regulating device is provided, which is integrated with the control device of the pump. For setting a desired fill pressure in the cuff of the tube introduced into the trachea of a patient, it is also proposed that a measuring and regulating device for the fill pressure be provided, which is integrated with the control device of the pump.

Material rising up into the pharynx from the stomach and intestinal tract represents, particularly for the unconscious patient being ventilated, a permanent reservoir of microbes, and may provoke or exacerbate pulmonary infection from the lower pharynx on intubation. Artificially ventilated intensive care patients are looked after through secretion-stimulating gastric probes or feeding tubes whose throughput as a rule is still insufficient to put a stop to gastro-esophogeo-pharyngeal reflux beside or along them. As a result the greater number of sedated or artificially ventilated patients are virtually overwhelmed by high-grade bacterially contaminated material in the pharyngeal, nasal and postnasal regions.

On account of various difficulties in the search for a simple mechanical esophageal or gastric blockade tolerable in the long term this infective problem potential could not until now be satisfactorily resolved. What was tried out therapeutically, and generally tolerated, was essentially medicinal/antibiotic (e.g. selective bowel decontamination).

Since the structures of the esophageal wall react extremely sensitively to persistent pressure or tension, the conventional blocking techniques, in which the walls of the attached structures are placed under tension (as a rule by a balloon) are not, or only with limitations, applicable in the case of the esophagus.

The esophagus is a dynamic structure constantly changing in shape. The tonus of its wall, and its lumen, are subject to considerable active and passive functional fluctuations. Tamponization of the oesophagus by a bladder like that of the invention fits in with their physiological dynamic and thus guarantees a simple self-regulating and well-tolerated closure or filling of the gullet. Regurgitation of material highly contaminated with microbes from the stomach and gut regions into the oral, nasal or pharyngeal cavities is prevented by the invention. By means of the invention gastro-esophageal-pharyngeal reflux is prevented by a simple self-regulating and well-tolerated mechanical blockade in the esophageal region. Drainage of stomach contents is thus guaranteed to take place through an ordinary stomach or feeding probe.

Ulcerations or necroses of the esophageal wall structures as a result of long-term blocking are excluded by the most far-reaching pressure-passive actions of the tampon-bladder described in the invention.

Immediately adjoining structures such as the great vessels, the accompanying nerves, the trachea and main bronchi, the lungs themselves and, not least, the heart, particularly the left atrium, are, in contrast to conventional blocking, not endangered.

Another medium which is distinguished by compressibility as well as a certain adaptability of its own to the fluctuations mentioned above is, for instance, a gaseous one. Filling apparatus, reservoir, equalizing vessel and pump may all be used with any suitable medium and are designed accordingly. Air is a preferred.

The inner cavity of the tampon-bladder may be filled with a medium, through a channel lying between the inner and outer lumina, from a filling device connected to the channel. Simply operated examples of such a filling device are a reservoir or equalizing vessel, particularly one situated outside the patient. A supply of the medium sufficient to fill the inner cavity of the tampon-bladder, and in addition to allow for the abovementioned functional fluctuations of the lumen and the tonus of the esophageal wall through further outflow or intake of the medium by expansion and collapse of the tampon-bladder, is kept in the reservoir or equalizing vessel. In this connection it could be seen as an additional advantage for the medium to be actively led into the inner cavity of the tampon-bladder or withdrawn from the inner cavity through the channel. Such active supply and withdrawal take place through a pump which is regulated preferably to compensate for any extensive pressure-passive fluctuations in the tampon-bladder. So that a medium is used which can be supplied or withdrawn rapidly and at the same time has a thermal capacity high enough for the adjustment of the temperature measured inside the esophagus, it can be a fluid such as for example water or equivalent. Such a medium is simple and quick to pump and easily adjustable in temperature.

FIG. 1, shows a schematic illustration in cross-section of a patient's torso. The patient's chest cavity wall 1, lungs 2, diaphragm 3, intra-thoracic space 4, esophagus 5, stomach 6 are depicted. The present feeding system, according to an embodiment, is also shown as it may operate in situ in a patient's thorax. The feeding pump system, as illustrated in FIG. 1, includes a combination of a naso-gastric tube 7 inserted through the nasal cavity, down the pharynx, esophagus, and terminating in the stomach. The naso-gastric tube has a sensor bladder or balloon situated near the end of its tip in the stomach. This gastric balloon 21, is connected by a filling line 13. Just outside of the stomach is situated an esophageal balloon 8 with a filling line 12 along the naso-gastric tube. A tube segment 9 to be inserted into a roller pump 10, or similar mechanism used in gastric feeding pumps 20 connects the system. The feeding pump or regulator mechanism has a display 19 with options for controlling or regulating the feeding rate and other parameters or feedback from sensors: change in pressure ($\Delta P$), actual volume/unit time (V/h), esophageal pressure ($P_{esophagus}$), gastric pressure ($P_{gastric}$), input mechanism option for ΔP 16, volume 17, and delivery time 18, connection to feeding container 11.

The present invention is a further advance upon a stomach probe as described in German Utility Model Application No. 202006002832.3, the contents of which are incorporated herein. The stomach probe has an esophageal bladder and enteral feeding tube that are integrated such that the feeding tube sits at or near the center of the bladder when used in a patient. The feeding tube as a thin-walled bladder associated with the feeding lumen. Around the feeding lumen is either one or a plurality of ferrules that are used to conduct air or other gas along the length of the bladder.

A stomach probe of this type has a lumen that is located on the delivery cannula in the region of the inflatable stopper, which guarantees a rapid equalization of volume between sections or partial volumes of the inflatable stopper. The lumen is arranged so that a channel is formed between the lumen and the delivery cannula, which is connected to the interior of the inflatable stopper via a number of openings, and which is arranged on the lumen. The interior of the inflatable stopper is connected to means for producing pressure in the inflatable stopper via the channel formed between the delivery cannula and the lumen. The lumen is thereby kept open by stent-like devices or spacers between an outer and an inner wall of the probe or the delivery cannula of the stomach probe. A stomach probe of this type is therefore much more complicated to produce than conventional stomach probes without a lumen, for example.

The object of the invention is to improve a stomach probe of the aforementioned type, in that the lumen, which is located between the delivery cannula and the inflatable stopper and which is connected to the interior of the inflatable stopper, can be produced by a relatively simple technique, and at the same time guarantees adequate volume equalization between the partial volumes of the inflatable stopper.

The separate shaped body can be produced by a simple technique, since it can be prefabricated as a separate component. During assembly of the stomach probe, it is mounted as a finished component on the delivery cannula, and attached to it. This simplifies assembly of the stomach probe, since the number of individual processing stages needed to produce the lumen can be reduced. This results in a potential for reducing both time and costs when producing the stomach probe. Applying the shaped body to the delivery cannula determines the shape of the lumen at the same time, which ensures that there is sufficiently rapid volume exchange between the sections of the inflatable stopper.

The shaped body may have a tubular structure, whose internal shape corresponds roughly to the external shape of the delivery cannula. The tubular structure enables the shaped body to be attached roughly concentrically to the delivery cannula. This simplifies the assembly process. The shaped body may have at least one opening which extends in roughly the longitudinal direction of the shaped body over at least 50 to 60%, preferably over up to 70%, and especially over up to 80%, of the total length of the shaped body, and joins the lumen with the interior of the inflatable stopper. This opening guarantees adequate volume equalization between different sections of the inflatable stopper. The opening may extend over roughly the entire length of the shaped body. The opening guarantees good volume equalization between the sections of the inflatable stopper, and can also be produced using simple techniques. The shaped body may have several wall elements extending radially in cross section which, at their outermost ends, have a surface extending roughly transversely to the relevant wall element. The surfaces extending roughly transversely to the wall elements provide a good contact surface for the inflatable stopper. The wall elements extending radially in relation to this guarantee that there is an adequate distance between the surfaces and the delivery cannula, and thus create a lumen that is large enough to guarantee good volume equalization. The size and number of the individual lumen sections can be defined as a function of the number of wall elements.

At least one of the wall elements may have a roughly T-shaped profile. This profile can be produced easily, and provides a lumen of sufficient size, as well as a good contact surface for the inflatable stopper. At least one of the wall elements may advantageously have a roughly L-shaped profile. This profile can also be produced using simple techniques, and provides for a lumen and contact surface that permits rapid volume exchange between the sections of the inflatable stopper.

In one embodiment of the invention, the cross section of the shaped body may have several wall sections, which are supported at the delivery cannula of the probe and, together with it, define at least one section of the lumen. These wall sections, which protrude inwards in a roughly finger-like arrangement, can form a passageway with their front ends, whose dimensions correspond approximately to those of the delivery cannula. The shaped body can therefore be mounted easily onto the delivery cannula.

The wall sections may extend in a roughly star-shaped configuration into the interior of the shaped body. This arrangement guarantees an approximately even distribution of the wall sections. This guarantees secure support and retention of the shaped body. The shaped body may have at least one spiral-shaped coil. This coil can be produced by a simple technique and can be mounted easily onto the delivery channel. Furthermore, it provides a sufficiently large lumen between the individual windings of the coil to guarantee good volume exchange.

A roughly tubular element can be arranged on the coil, which has several openings distributed over its surface. This enlarges the contact surface for the inflatable stopper. The tubular element may be formed as a net-like construction. This net-like construction can be produced efficiently and can be premounted onto the coil. This can simplify assembly.

The shaped body may have one or several layers comprising a net-like construction. The individual openings in the net-like structure, or their overlapping points, define a sufficiently large lumen, which permits good volume exchange between the sections of the inflatable stopper.

The lumen in the region of the axial front side of the shaped body may expediently be connected to a delivery channel, via which the inflatable stopper can be filled with a fluid. This can be produced using simple techniques and simplifies the construction of the stomach probe, since the inflatable stopper can be filled directly via the lumen with which it is connected.

The shaped body may be made from PVC, PUR, blends of PVC and PUR, blends of PUR and polyamides, and/or silicone. These materials guarantee good compatibility. They can be shaped easily and thus reduce the risk of injury during introduction of the probe, yet they are stable enough to maintain the lumen.

The shaped body may be produced by extrusion. This manufacturing process enables the shaped body to be produced by a relatively simple and quick technique. Alternatively, the shaped body can be fixed by means of friction onto the delivery cannula. This determines the position of the shaped body relative to the delivery cannula. The shaped body may be fixed by means of a press-fitting action onto the delivery cannula. This guarantees axial and/or radial fixing of the shaped body on the delivery cannula of the stomach probe.

The shaped body may be fixed by means of adhesion to the delivery cannula. This simple adhesive technique guarantees adequate fixing of the shaped body. The shaped body may be fixed by means of a material-bonding action to the delivery cannula. This guarantees a high-quality bond between the shaped body and the delivery cannula. The shaped body may be joined to the delivery cannula, at least in parts, by a solvent. Solvent etching of the shaped body, and/or the delivery cannula, at least in parts, guarantees good bonding of the two components.

The outer diameter of the shaped body may be approximately between 7 and 12 mm, and especially between 6 and 8 mm. These dimensions guarantee good volume exchange between the sections of the inflatable stopper. The length of the shaped body may advantageously be approximately between 6 and 12 cm, and especially between 6 and 9 cm. These lengthwise dimensions have proven to be advantageous. They provide a sufficiently large contact surface for the inflatable stopper. At the same time, an adequate volume exchange between all the sections of the inflatable stopper is guaranteed. The stomach probe may be provided with at least one radiopaque marker. The marker, which may be a metal ring, for example, facilitates positioning of the probe in the patient and acts as a reference point to orientating organs, such as the diaphragm and/or hyoid, on the X-ray image of the thorax.

Figure 2:
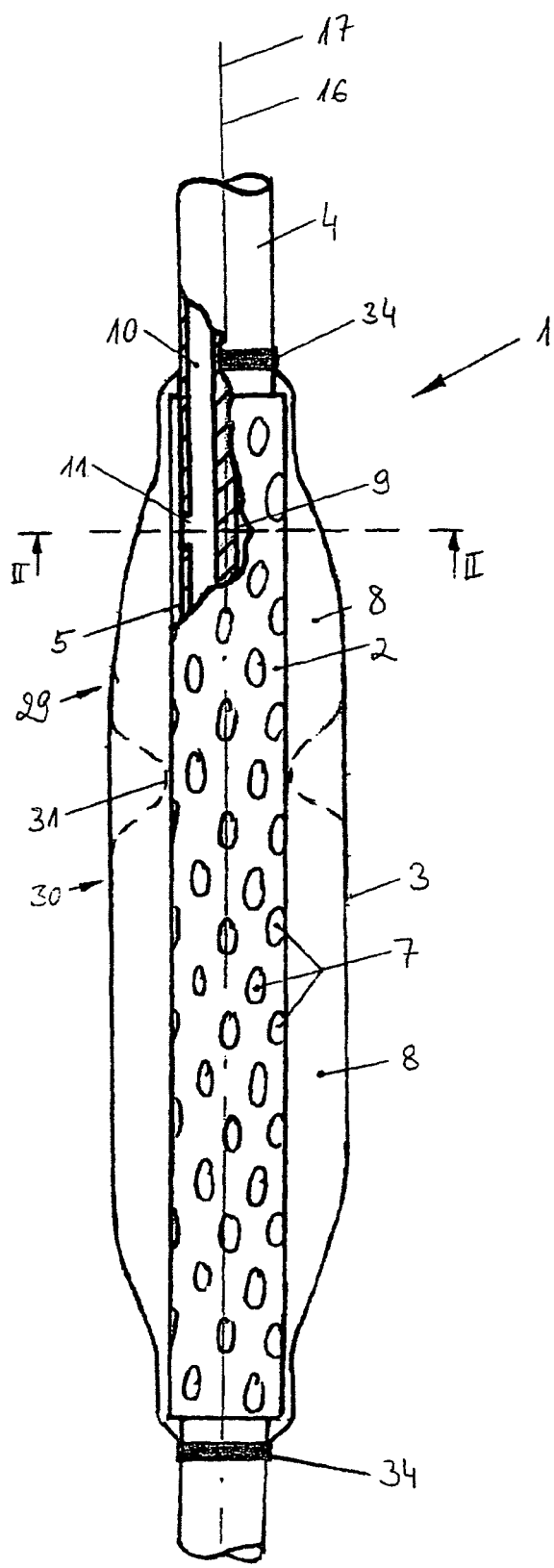
FIG. 2 is a partial cut-away illustration of an embodiment of the esophageal bladder device and feeding tube according to the present invention.
Figure 3:
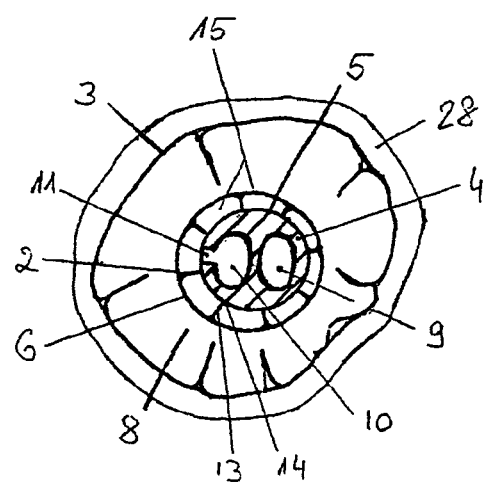
FIG. 3 is a cross-sectional view of the device shown in FIG. 2, along line II-II, as it may sit in the esophagus.

FIG. 2 illustrates the basic construction of an anti-gastric reflux esophageal-stomach probe 1 according to the present invention. A shaped, conduit body 2 is superimposed around and over a delivery cannula 4 in the region of an inflatable bladder 3. The conduit body 2 encloses a lumen 5 in its interior. The lumen 5 is shown in FIG. 3, and represents the cross section A-A through the stomach probe shown in FIG. 2. In this example of the embodiment, the lumen 5 is located between the delivery cannula 4 and the surface 6 of the conduit body 2. As can be seen in FIG. 2, the shaped body 2 has several openings 7, which are distributed over the entire surface 6 of the shaped body 2. The lumen is connected to the interior 8 of the inflatable stopper 3 via the openings 7. This means that the openings 7 permit volume or fluid exchange between the lumen 5 and the interior 8 of the inflatable stopper 3.

The number and shape of the openings 7 may vary, depending on the end use. In addition to the approximately round or oval openings 7 shown here, the openings may also be elongated, for example. The shape or contour of the openings 7 may vary from being a largely round or oval cross-sectional profile, to triangular, quadrangular or polygonal openings. Nor do the openings have to be distributed more or less evenly over the surface 6 of the conduit body 2 as in this case. Alternatively, the openings 7 may also be distributed unevenly. In this case, it is important that the shape and arrangement of the openings permit adequate volume exchange between two sections, 29 and 30, of the inflatable stopper 3. The number of openings may vary from one to any number of individual openings, e.g. 100 or 1000 openings. The number is restricted only by the area of the surface 6 of the conduit body 2 and the shape of the openings.

The outer diameter of the delivery cannula 4 is advantageously between 3 and 6 mm, and especially between 4 and 5 mm. In the interior, in addition to a channel 9, which provides the patient with liquid nutrients, there is a delivery channel 10, via which the inflatable stopper 3 can be filled with a fluid, such as water. Different fluids may be used, depending on the application, e.g. gas or gas mixtures, such as air, or viscous liquids. The diameter of the inflatable stopper 3 in a freely unfolded condition is between 20 and 50 mm approx. A diameter of 30 to 40 mm is particularly favorable. In this embodiment, the delivery channel 10 for the fluid extends, at least in parts, into the conduit body 2 and has an access opening 11 running radially in relation to the shaped body 2, which connects the delivery channel 10 to the lumen 5.

Figure 5:
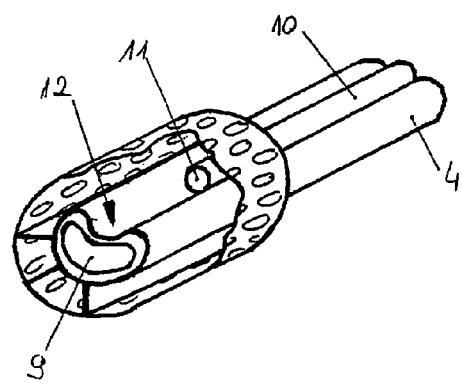
FIG. 5 shows a perspective view of a delivery cannula.

In other embodiments of the disclosed stomach probe 1, the delivery channel 10 may also run along the outside of the delivery cannula 4. It may, for example, be located, at least partly, in an indentation 12, which runs along the delivery cannula 4, as FIG. 5 shows. The access opening 11 of the delivery channel 10 does not necessarily have to run radially, but may also run in the region around the axial front surface of the shaped body 2 than axially to the shaped body 2.

Figure 4:
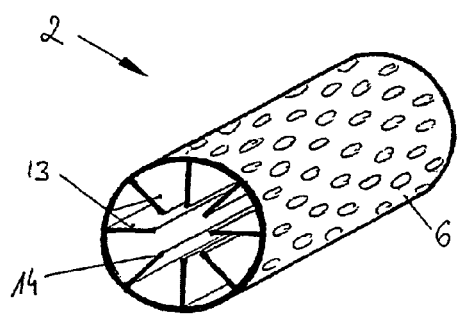
FIG. 4 shows a perspective view of a shaped body shown in FIGS. 2 and 3, according to a first embodiment.

FIG. 4 shows an enlarged image of the disclosed shaped body 2 as shown in the first embodiment of the invention. The shaped body 2 has a total length of roughly 6 to 9 cm, and has an almost cylindrical external shape. Several wall sections 13 extend radially from the cylindrical surface 6 into the interior of the shaped body 2. The free, front ends 14 of the wall sections 13 define a diameter, which corresponds approximately to the outer diameter of the delivery cannula 4. In the state in which it is used, i.e. when the shaped body 2 is located on the delivery cannula 4, the front ends 14 of the wall sections 13 rest on the delivery cannula 4, as FIG. 3 shows. Together with the delivery cannula 4, the lumen 5 inside the shaped body 2 is divided into separate lumen sections 15. A single lumen section 15 is delimited by two wall sections 13, the section of the surface of the shaped body 6 which lies between the two wall sections 13 and the section of the surface of the delivery cannula which is located between the contact surfaces of the front ends 14 of the wall sections 13. In this example of the embodiment, the shaped body 2 has eight wall sections, which all extend in a finger-like manner by roughly the same amount into the shaped body. In other embodiments of the invention, the number of wall sections, however, may vary arbitrarily, and thus influence the shape of the lumen 5 or the individual lumen sections 15. The depth to which the wall sections 13 penetrate into the interior of the shaped body 2 may also vary, and this determines the position of the shaped body 2 in relation to the delivery cannula 4. This means that the shaped body 2 does not necessarily have to sit more or less concentrically on the delivery cannula 4 as shown here. Depending on the particular application, the longitudinal axis 16 of the shaped body 2 may also be displaced in relation to the longitudinal axis 17 of the delivery cannula 4.

Figure 6:
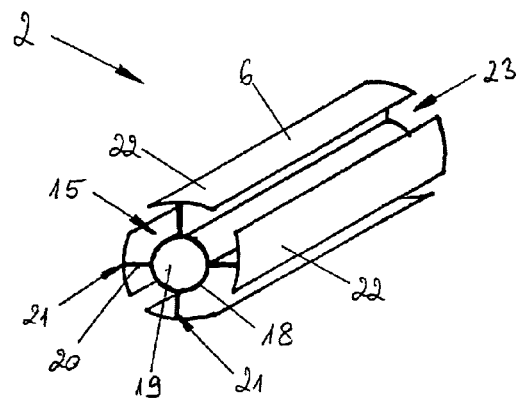
FIG. 6 shows a perspective view of a disclosed shaped body according to a second embodiment.
Figure 7:
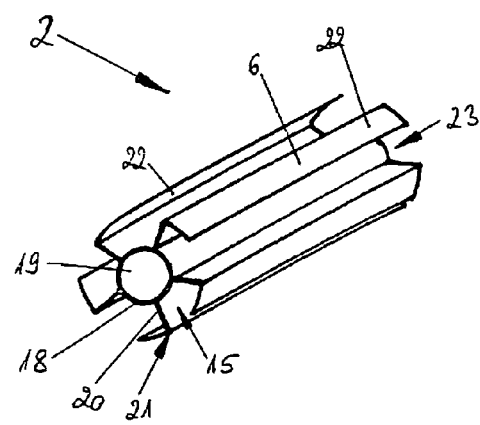
FIG. 7 shows a perspective view of a disclosed shaped body according to a third embodiment.

FIGS. 6 to 9 show perspective views of further embodiments of the disclosed shaped body. FIGS. 6 and 7 show second and third embodiments of the disclosed shaped body 2. The reference numbers used in FIGS. 2 to 5 refer to the same components as those in FIGS. 6 and 7. The shaped bodies 2 have a central, roughly tubular structure 18, with a roughly circular cross section. The shape of the inner cover surface 19 roughly corresponds to the shape of the surface of the delivery cannula 4. Several wall elements 20 extend radially outwards from the central, tubular structure 18. At the outermost end 21 of each wall element 20 lying opposite to the central, tubular structure 18 is a surface 22, which runs roughly transversely to the wall element 20.

In FIG. 6, the shaped body 2 has four wall elements 20 arranged roughly in a circle. The wall elements 20, together with the associated surfaces 22, form an approximately T-shaped profile in the cross section. The shaped body 2 in FIG. 7 has five wall elements 20 arranged in an approximate star-shaped configuration around the tubular structure 18.

The wall elements 20, together with their respective transverse surfaces 22, form a roughly L-shaped profile in cross section.

The T- and L-shaped profiles of the shaped bodies 2 shown in FIGS. 6 and 7 are located at such a distance from each other, or are dimensioned in such a way, that the transverse surfaces 22 of two adjacent T- or L-shaped profiles are at a distance from each other. This means that every two of the transverse surfaces 22, which form the surface 6 of the shaped body 2, define an opening 23 or slit, which runs along the length of the shaped body 2. In these examples of the embodiment, the lumen 5, which is located here between the transverse surfaces 22 and the tubular structure 18, is divided by the T- or L-shaped profiles into separate lumen sections 15. The shape of an individual lumen section 15 is thereby determined by in each case two adjacent T- or L-shaped profiles and the section of the surface of the tubular structure 18 enclosed by them.

The number of wall elements 20 may be varied, depending on the end use. If this changes, the shape and the number of lumen sections 15 and openings 23 in the surface 6 of the shaped body 2 also change. In a further embodiment of the invention, the wall elements 20 may also be arranged unevenly around the tubular structure 18, unlike the examples shown here. The transverse surfaces 22 at the ends 21 of the wall elements 20 can also be dispensed with. In this case, the surface 6 of the shaped body 2 is determined by the ends 21 of the wall elements 20. The number of wall elements 22 may be increased accordingly, and there may be between 5 and 15 wall elements, for example.

Figure 8:
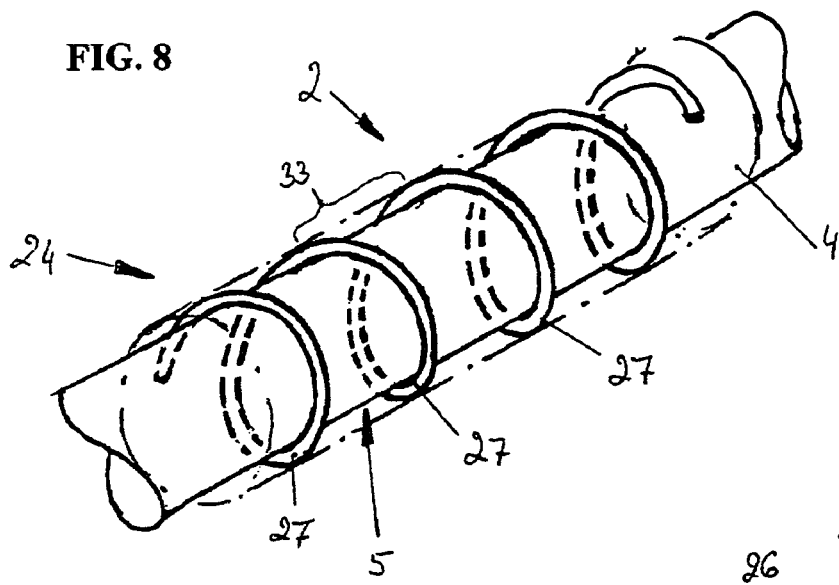
FIG. 8 shows a schematic is an alternative design for the ferrule

FIG. 8 shows a further embodiment of the disclosed shaped body 2. In this case, the shaped body 2 is in the form of a spiral and is formed as a coil 24. The inner diameter of the coil 24 corresponds approximately to the outer diameter of the delivery cannula 4. In this embodiment, the lumen 5 also has a spiral shape. In use, that is when the shaped body 2 is located on the delivery cannula 4, as shown in the diagram, the windings 27 of the coil 24 define an opening 33, which runs spirally around the delivery cannula 4, between the individual windings 27 of the coil 24, and encloses the lumen 5. The thickness of the coil 24 determines the height of the lumen 5. The product may have a roughly circular cross section. However, alternatively, it may have an oval or angular shape.

In a further embodiment, the lumen may also be defined by several, for example, two coils, which are pushed roughly concentrically so that they are on top of each other. In this case, the two coils may have the same or different gradients. The coils may also be superimposed so that they run in opposite directions. In this case, the lumen 5 is defined by the intermediate space between the individual windings of the relevant coil, i.e. by the overlapped sections of these intermediate spaces.

In addition to single or interconnected coils, a pipe-like or tubular structure can also be applied, which has openings and which is shown in FIG. 8 by a line consisting of a sequence of dots and dashes. The external shape of this type of shaped body would then be similar to the shaped body shown in FIG. 2.

The abovementioned first to third embodiments of the disclosed shaped body 2 can also be twisted, rather like a screw, and are thus shaped like a coil.

Figure 9:
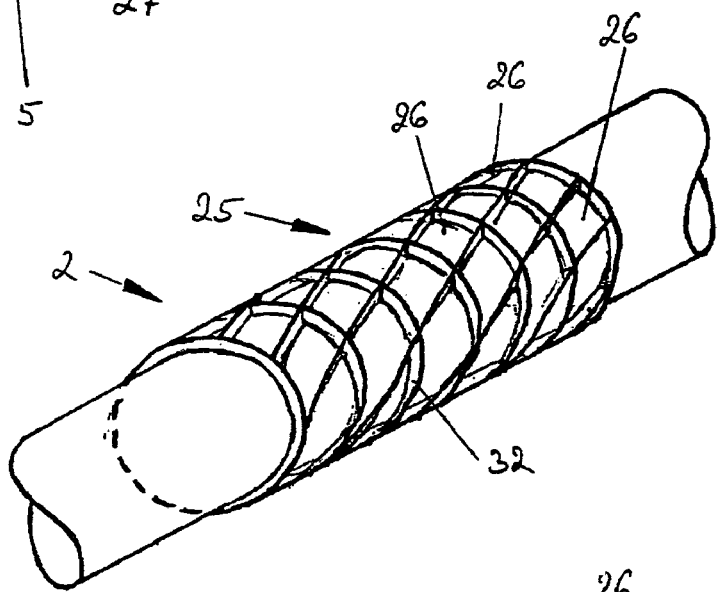
FIGS. 9 and 9*a* shows a variation of the design of FIG. 8.

FIG. 9 shows a fifth embodiment of the disclosed shaped body 2. It is pipe-like or tubular in shape and has a net-like construction 25. The inner diameter of the shaped body 2 corresponds approximately to the outer diameter of the delivery cannula 4. In this case, the lumen 5 is located within the mesh or openings 26 of the net-like construction 25, which are at least partly connected to each other, and thus permit volume exchange between the individual openings 26 of the net-like construction 25.

Figure 9A:
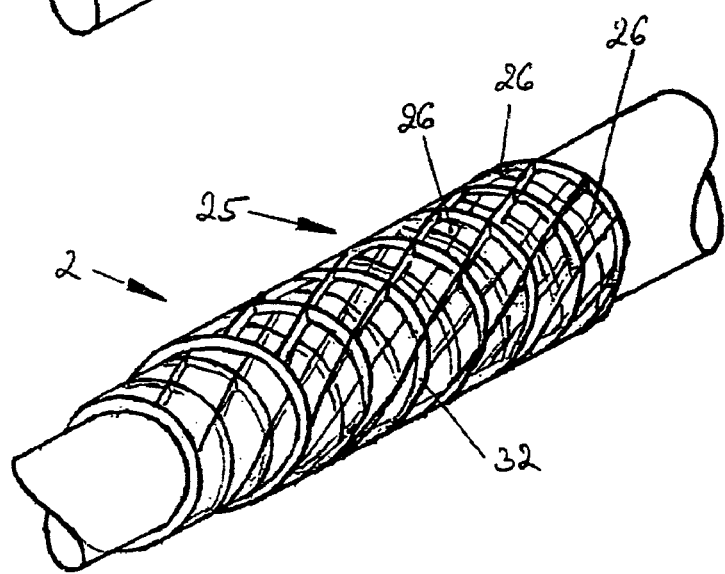

In a further embodiment of the invention, the shaped body 2 may also comprise several layers of the net-like construction 25, as FIG. 9a shows. These are arranged roughly concentrically in relation to each other, whereby the inner diameter of the innermost layer corresponds approximately to the outer diameter of the delivery cannula 4. In this case, the lumen 5 is defined by the holes 26 in the net-like construction 25, which overlap at least in parts. This means that the overlapping holes 26 of the individual layers of the net-like construction 25 form channels or individual lumen sections 15. When the shaped body 2 is in the state it is in during use, i.e. when it is located on the delivery cannula 4, at least part of the lumen section 15 extends at least in sections along the delivery cannula 4, and thus permits volume exchange between the individual sections of the inflatable stopper 3.

The dimensions of the different embodiments of the shaped body 2 described here may vary, depending on the end use. In practice, however, an approximate length of 6 to 12 cm, and especially a length of 6 to 9 cm, has proved to be particularly advantageous for the shaped body 2. The outer diameter also depends on the end use, as well as on the dimensions of the delivery cannula 4 and the inflatable stopper 3, and is advantageously in the region of between 7 and 10 mm, and especially between 6 and 8 mm. For special end uses, however, the dimensions of the shaped body 2 may deviate from the abovementioned dimensions.

The shaped body 2 described in embodiments 1 to 5 is preferably made from plastic and is produced by an extrusion process. Alternatively, the shaped body may also be produced by casting or injection molding. In principle, the materials used for the shaped body 2 are ones which can deform easily to suit the human body, i.e. they do not injure the patient whilst being inserted or during long-term use of the probe, but they are rigid enough to provide a non-collapsible shape when peristalsis occurs over the shaped body 2. Advantageous materials are, for example, PVC, PUR, blends of PVC and PUR, blends of PUR and polyamides, and silicones.

To improve orientation, the stomach probe may be fitted with radiopaque markers, such as metal rings 34 or similar devices, as shown in FIG. 2. These may be placed at the shaped body 2, the delivery cannula 4 and/or the inflatable stopper 3.

The functions of the embodiments shown in the figures will now be explained. When assembling the disclosed stomach probe 1, the shaped body 2 is applied to the delivery cannula 4, e.g. by means of a sliding process. Since the inner diameter of the relevant shaped body 2 corresponds approximately to the outer diameter of the delivery cannula 4, or is at least slightly smaller than it, a slight press-fitting effect occurs during mounting of the shaped body 2 onto the delivery cannula 4. The resulting static friction fixes the shaped body 2 radially and axially onto the delivery cannula 4.

The shaped body 2 may also be fixed onto the delivery cannula 4 by means of adhesion, e.g. by applying an adhesive at least on part of the contact surface between the shaped body 2 and the delivery cannula 4.

Alternatively, the shaped body may also be fixed by material-bonding whereby, for example, at least part of the contact surface between the shaped body 2 and the delivery cannula 4 is treated with a solvent. In principle, any possible combination of the abovementioned fixing techniques are feasible as a means of attaching the shaped body 2 onto the delivery cannula 4. With the shaped body 2 shown in FIGS. 2 to 4, the inner diameter of the shaped body 2 and the contact surface between the shaped body 2 and the delivery cannula 4 is formed by the front ends 14 of the wall elements 13. When mounting the shaped body 2 onto the surface of the delivery cannula 4, these are arranged so as to divide the lumen 5 inside the shaped body 2 into individual lumen sections 15, as FIG. 3 shows.

With the embodiments of the shaped body 2 shown in FIGS. 6 and 7, the inner diameter of the shaped body, as well as the contact surface between the shaped body 2 and the delivery cannula 4, are formed by the tubular structure 18.

With the coil 24, the fourth embodiment of the shaped body 2 shown in FIG. 8, the inner diameter of the shaped body 2 is determined by the inner diameter of the coil 24. The contact surface between the shaped body 2 and the delivery cannula 4 corresponds, in this case, to the spiral installation line or surface of the individual windings 27 of the coil 24. Whether it is in the form of a line or a planar configuration will be determined by the cross section of the coil.

With the fifth example of the embodiment of the shaped body 2 shown in FIG. 9, the net-like construction 25, the inner diameter of the shaped body 2 and the contact surface between the shaped body 2 and the delivery cannula 4 are determined by the individual connecting pieces 32 of the net-like construction 35.

The final, assembled stomach probe is used for treating comatose patients, for example, who are unable to feed themselves. In this case, the disclosed stomach probe 1, i.e. the delivery cannula 4 of the stomach probe 1, is inserted into the patient's esophagus, whereby the section of the stomach probe that is fitted with the inflatable stopper 3 is located above the entrance to the stomach in the esophagus. The preferable length of the shaped body 2 of approximately 6 to 9 cm ensures that it fits well in the section between the upper and lower sphincter of the esophagus. The radiopaque marker 34 makes it possible to check that the probe is in the correct position by means of an X-ray image. The inflatable stopper 3 is filled with a fluid, e.g. water, via the delivery channel 10, whereby the fluid flows through the access opening 11 of the delivery channel 10 into the lumen 5 of the shaped body 2. The fluid flows into the interior 8 of the inflatable stopper 3 through the openings 7, 23, 26 and 33 of the shaped body 2. As it fills with the fluid, the inflatable stopper 3 expands until it lies almost completely against the wall of the esophagus 28, as can be seen in FIG. 3. This enables the esophagus 28 to largely be sealed off from liquids or solid substances, which tend to move up from the region of the stomach towards the pharyngeal cavity, and thus to keep the windpipe free from harmful substances.

The swallowing motions made by the patient who has been fitted with the disclosed stomach probe cause the muscles to contract along the esophagus. These create one or usually several annular constrictions in the esophagus, which are propagated from the larynx region towards the stomach, i.e. along the esophagus.

In order to illustrate the functions of the shaped body 2, the movement of a single, annular constriction will now be examined. In the area around the inflatable stopper, the annular constriction causes a partial reduction in the outer diameter of the inflatable stopper 3, i.e. a local narrowing 31 of the inflatable stopper 3 occurs, which is shown in FIG. 2 as a dotted line. This divides the inflatable stopper into two sections, 29 and 30. While the constriction 31 moves along the inflatable stopper 3, the dimensions of the individual sections, 29 and 30, change. In this case, however, the volume of fluid, which can be contained in the relevant sections, 29 and 30, of the inflatable stopper 3, changes. The disclosed shaped body 2 provides a lumen 5, which permits rapid volume exchange between the individual sections, 29 and 30, of the inflatable stopper 3. The surface 6 of the disclosed shaped body 2 provides, if necessary, a contact surface for the constricted wall section of the inflatable stopper 3. The lumen 5 is therefore kept free of these external influences, and is available entirely for volume exchange. While the constriction 31 moves along the inflatable stopper 3, the fluid is forced out of the interior 8 of section 29 of the inflatable stopper 3 via the openings 7, 23, 26 and 33 and the lumen 5 is forced into the interior 8 of section 30 of the inflatable stopper 3.

As part of the system, the present invention has associated hardware units. The one unit is an air pump for controlling the relative dynamic pressure within the esophageal bladder. A second unit is a gastric feeding pump for regulating the rate of feeding. The air pump may inflate or deflate the esophageal bladder according to certain set parameters. The air pump may be operated by means of either a preprogrammed automatic function or adjusted manually by a clinician or healthcare staff, depending on the clinical situation and need, or both. The units can be used either separately in individual modules or integrated together in a single device. Unlike, conventional gastric feeding pumps, which do not have the ability to monitor or regulate intra-gastric pressure, modulate the feeding rate based on the sensed intra-gastric pressure, or counterbalance the gastric pressure with an esophageal sealing mechanism to prevent gastric reflux, the present invention can perform all three functions when the two units are integrated in a single device. This combination in a single device can be a great advantage and improvement over the existing feeding pumps.

The outer surface of the esophageal balloon, in some embodiments, may be treated with either buffering agent that can neutralize a small quantity of stomach acid that may seep up in between the balloon and esophagus wall. Additionally, the balloon surface may also be treated with an anti-microbial coating that minimizes the growth of bacteria.

A technique to seal off a natural or artificial body compartment or bladder that has or is kept at a sealing pressure. The esophageal balloon should be sufficiently large enough to seal the entire passage way of the esophagus. The balloon has a residual diameter that is larger than the diameter of the esophagus when it is distended or expanded to its full internal diameter.

The esophageal balloon is pre-shaped and has a number of pleats that enable it to intermesh or fit with the folds of the esophagus lining, and prevent any gaps forming between the thin membrane skin of the balloon and the esophagus lining.

Algorithmic Control

Analogous to a ventilation control technique, such as described in U.S. Pat. No. 7,040,321 B2, which is incorporated herein by reference, the present enteral feeding pump also uses an algorithmic control. After placement of a gastric probe and activation of the device, the regulator pumps a defined volume into the gastric balloon to fill the bladder, which is preferably smaller than the volume of the gastric balloon itself in its freely inflated preshaped state. Once the pressure within the bladder reaches a stable reading of the intra-gastric filling pressure (i.e., a mean pressure level derived through an averaging process), the esophageal seal pressure is regulated at a predetermined value that is preset in a computer software used to monitor and control the pump, or that can be defined by a user. The user would have to enter a desired value for a range or limit for change in pressure ($\Delta P$), affecting the esophageal pressure parameters, which can be calculated thus: gastric pressure+$\Delta P$ value. As the pressure in the gastric balloon is adjusted to compensate for change in pressure and conditions in the abdominal and thoraxic cavities arise over the course of enteral feeding, one can ensure that the esophageal balloon remains in place and stationary with the initial filling volume.

Due to the particular membrane characteristics of the foil of the sealing esophageal balloon, a hydrostatic pressure gradient of about 10-25 cm of water is considered to produce a reliable seal against passive reflux of gastric contents. Typically, a hydrostatic pressure of up to about 12 or 15 cm to 20 cm is employed. The present pump permits the user to enter a desired feeding volume to be administered over a certain timer period, whereby volume and time values can be separately defined and programmed to achieve the desired feeding regime.

Through appropriate associated computer software, the pump determines the actual rate of feed volume delivered over a primary feeding interval (e.g., about 15 minutes). The pump has a visual display that shows the resulting calculations (Volume/time). A user may enter a desired feeding duration and calculate the volume delivered within an hour (V/h), or over the entire feeding period selected. With appropriate software, one can condition the pump to be a "smart" device that, over the course of use, can "learn" the desired or predetermined feeding functions. The feeding pump will sense and adjust the amount of pressure not only in the stomach but also the esophagus. That is, the pump will have a memory system that enables it to apply a certain software preset or user defined feeding rate (i.e., feed volume over a certain preset time interval) to determine the compliance of a patient's stomach against the feed volume. Based on the pressure increase over the applied volume, the slope of the determined graph (V/P) can be automatically increased in order to reach a desired volume (V/$t_{total}$), in particular for extended feedings.

If the feeding solution pumped into the patient's stomach causes an increase of intra-gastric pressure, the pressure in the esophageal balloon is adjusted with a corresponding increase in ΔP. To prevent an uncontrolled increase in the pressure in the esophagus ($P_{esoph.}$), a maximum pressure ($P_{max}$) value for the esophagus relative to the gastric pressure, which is not to be exceeded, can be set by a user or the computer software, respectively. An upper pressure reference point for the esophageal balloon seal should be a value that is considered to be tolerable by the esophagus walls, and does not cause tissue or other structural damage (e.g., distension) to the organ after exposure to the elevated pressure force that seals the esophagus over a protracted time period. The maximum gastric pressure can be calculates as: max $P_{esoph.}$–set ΔP. Once the maximum gastric pressure is reached under a certain parameter setting, the feeding pump will stop and wait until the intra-gastric pressure has sufficiently decrease to within normal feeding levels before starting feeding again. The hourly and expected feeding volumes over the selected time period can be calculated and determined continuously, by continuous sensing and regulation of intragastric pressure.

According to the present invention, the gastric pressure can be sensed by means of either a balloon that is incompletely filled (e.g., up to about 75-80% of the volume in free inflation without hull distension), or an electronic sensor element. The signal received can be averaged, a filter algorithm built in. Based on the averaged value, a user set gradient value is added to the actual gastric pressure, thereby defining the esophageal seal pressure. The seal pressure can be further defined by a default minimum pressure (e.g., 10 mbar) and a default or user determined maximum pressure (one that is considered perfusion critical, e.g., 50 mbar, when exerted over a period of more than 5 hours).

Similar to a computer program-assisted control, the feed pump can be operated using gravity. Instead of an electronic occlusion element that interrupts or gradually controls the flow of feeding solution, in a gravity-operated pump, once the critical intra-gastric maximum pressure value is reached, or the desired volume over time is reached. The controlling or steering software should be "smart." That is, it should be able to optimize the volume uptake of enteral feeding into the patient stomach. The user defines a desired delivery rate, by for example, independently setting volume and time period (e.g., 300 ml over 2 hours). The software then suggests a volume over 15 minutes, the pump delivers the requisite volume amount and determines the relative slope of gastric pressure. When the slope is in accordance with the calculated "ideal" slope, the parameters stay constant. After every interval a slope is determined.

When the slope is smaller than ideal, the algorithm then suggests a new slope, whereby the delivered volume over 15 minutes might be calculated on the basis of ⅔ of max esophageal pressure defined. When the slope is larger, volume per 15 minutes is reduced to a degree, that ⅔ of max esophageal seal pressure is likely to be reached. The relative levels of either gastric or thoracic pressure can be individual to each person.

Gravity-Operated Feeding Control

The present invention can operated according to either gravity (i.e., without a pump) or pump-operated concept. Both the gravity and pump-operated concepts are adapted for use in combination with a special balloon equipped nasogastric tube. When using gravity, the device is generally similar to that already described but, instead of a pump, the system integrates an electric occlusion element, which interrupts or gradually controls the flow of feeding, once the critical intra-gastric maximum pressure value is reached, or a volume flow over time has been reached, which exceeds the according outflow of feeding from the stomach into the small intestine and other lower portions of the gastro-intestinal tract.

A conduit around the feeding tube channels the air or other gaseous medium filling the esophageal bladder to be redistributed with each wave of a peristaltic contraction. Air baffles to help direct and regulate the air or other gaseous medium such as shown in accompanying FIGS. 4-7.

An inflated esophageal balloon significantly delays and decreases the magnitude of both GOR and bronchial aspiration of gastric contents when compared to the effect of a semi-recumbent position only. The inflated esophageal balloon imparts a protective obstructive effect on GOR in patients receiving mechanical ventilation.

The device can be used in combination placing the patient in a semi-recumbent position to prevent VAP. The role of the esophageal balloon can be even more relevant in patients who require a mandatory supine position (e.g., shock), receiving paralyzing or sedative agents, or show decreased abdominal compliance or gastroparesia for various reasons during mechanical ventilation.

It is desirable to maintain a low viable field pressure such that the bladder does not overly distend the esophageal wall and adversely impact its organic motility of the longitudinal enfolding.

The regular processing of food and stomach contents downwards from the thoracic to the abdominal cavity can be affected by the relative pressures within each cavity. The present invention functions in part on the principle of a balancing the transdiaphramatic pressure gradient, such that stomach contents are not allowed to reflux and overflow into the upper esophagus and pharynx.

Since the structures of the esophageal wall react extremely sensitively to persistent pressure or tension, the conventional blocking techniques, in which the walls of the attached structures are placed under tension (as a rule by a balloon) are not, or only with limitations, applicable in the case of the esophagus.

A healthy esophagus at rest has a residual dimension that has a number of enfolds that ripple along the esophagus wall surface. The present bladder has a diameter that is significantly larger than the dimensions of a normal extended esophagus. This design causes the bladder's thin membrane to have pleats that adheres closely to the surface of the esophagus and enfolds with the esophageal wall structures without distending the esophagus. As the esophageal wall changes conformation as a result of peristalsis, the membrane moves with the surface structures. The bladder functions as a tempenate with no or low tension against the esophageal wall, which occludes the passage way.

The present enteral-feeding tube design alleviates the disadvantages and permits one to close off or fill the esophagus without causing deleterious effect on the esophageal wall structures.

The esophagus is a dynamic structure that constantly changes in shape. The tonus of its wall, and its lumen, are subject to considerable active and passive functional fluctuations. Tamponization of the esophagus by a bladder like that of the invention fits in with their physiological dynamic and thus guarantees a simple self-regulating and well-tolerated closure or filling of the gullet. Regurgitation or reflux of material highly contaminated with microbes from the stomach and gut regions into the oral, nasal or pharyngeal cavities is prevented by the invention, which provides a simple self-regulating and well-tolerated mechanical blockade in the esophageal region. Control of the amount of pressure within the esophageal bladder counter balance with the relative pressure in the stomach and thoracic cavity ensured that stomach contents drain or exit through an ordinary stomach or feeding probe.

The particular pleated form of the esophageal bladder or balloon tends to reduce any occurrence of ulcerations or necroses of the esophageal wall structures as a result of long-term blocking. The pleats of the tampon-bladder are pressure-passive and intermesh with the esophageal lining. In contrast to conventional blocking, a relatively low pressure is maintained in the bladder, which does not harm immediately adjoining body structures and organs, such as the blood or lymph vessels, accompanying nerves, the trachea and main bronchi, the lungs themselves and the heart, particularly the left atrium.

The inner cavity of the tampon-bladder may be filled with the medium, through a channel situated between the inner and outer lumina, from a filling device connected to the channel. Desirably, the medium is a gas—air or some inert gas. Simply operated examples of such a filling device are a reservoir or equalizing vessel, particularly one situated outside the patient. A supply of the medium sufficient to fill the inner cavity of the tampon-bladder, and in addition to allow for the abovementioned functional fluctuations of the lumen and the tonus of the esophageal wall through further outflow or intake of the medium by expansion and collapse of the tampon-bladder, is kept in the reservoir or equalizing vessel.

In this context, an additional advantage would be for the medium to be actively led into the inner cavity of the tampon-bladder or withdrawn from the inner cavity through the channel. Such active supply and withdrawal take place through a pump which is regulated preferably to compensate for any extensive pressure-passive fluctuations in the tampon-bladder.

So that a medium is used which can be supplied or withdrawn rapidly and at the same time has a thermal capacity high enough for the adjustment of the temperature measured inside the esophagus, it can be a fluid such as for example water or equivalent. Such a medium is simple and quick to pump and easily adjustable in temperature.

Another medium which is distinguished by compressibility as well as a certain adaptability of its own to the fluctuations mentioned above is, for instance, a gaseous one. Filling apparatus, reservoir, equalizing vessel and pump may all be used with any suitable medium and are designed accordingly.

The present invention employs a probe, such as described in U.S. Pat. No. 6,551,272, for sealing an esophagus of a patient so that physiological shaping and function of the esophagus is not compromised. The probe has a tampon-bladder that is formed from a flexible and/or elastic material and forms an inside space for the reception of a medium. The tampon-bladder conforms to the pleatings of the esophageal wall structures when placed in the esophagus. A first lumen extends through the tampon-bladder, and a second lumen reaches into the tampon-bladder. The second lumen includes a channel for communicating with an inner cavity of the tampon-bladder. One can fill the inner cavity of the tampon-bladder through the channel using a filling device, such as a pump, that can be connected to the channel. The filling device ensures a slight, shape-maintaining filling pressure inside the tampon-bladder. A wall of the second lumen has a plurality of openings connecting an interior of the tampon-bladder with an interior of the second lumen. The openings are sieve-like, and are arranged over the length of the second lumen. The openings have a sufficient size and are in numbers along the tampon bladder length and diameter to enable a rapid exchange of volume of the medium between contracted and relaxed sectors of the tampon-bladder with each wave of peristaltic contractions of the esophagus.

The filling device has a reservoir or pressure equalizing device for the medium above the tampon-bladder, comprising a fluid column communicating with the interior of the tampon-bladder and adjusting a pressure in the tampon-bladder. The equalizing device has at least one reservoir with an inner cavity in communication with the tampon-bladder. The inner cavity is closed by a flexible or elastic wall at least in a sector thereof. The reservoir or equalizing device provides a means for adjusting a prescribed pressure in the tampon-bladder.

According to the invention, the tampon-bladder is part of a closed fluid system. The medium is a fluid, desirably a gaseous medium. In most embodiments, the tampon-bladder usually has a length of about 12-25 cm, desirably about 15-20 cm. The thin membrane wall of the tampon-bladder has a plurality of folds, which conform to the enfolding and torquing features of the esophageal wall structures.

The first lumen is arranged relative to the second lumen in a manner that the channel is formed between the first and second lumen. The second lumen is positioned relative to the first lumen forming the actual probe by means of baffle-like structures that bridge the passageway or dividing fixtures.

A pressure measuring probe includes a measuring end which is located in the tampon-bladder or in a cavity communicating with the inner cavity of the tampon-bladder. The stomach probe can be formed by a measuring-tube which forms the measuring end at its open end and at the other end, extracorporeally, incorporates a pressure-sensor or a pressure-transducer, and that the measuring-tube is filled with the fluid in such a way that the whole channel of the measuring-tube between the two ends is filled with fluid.

The gastric balloon or electronic monitor device at the end of the enteral feeding tube senses and measures the intragastric pressure. The monitor device continuously measures gastric pressure to generate a pressure gradient. Manual adjustment of the interval duration input to control feeding.

The present invention has been described in detail by way of examples. Persons skilled in the art, however, may appreciate that modifications and variations may be made to the present system and devices without departing from the scope of the invention, as defined by the appended claims and their equivalents.

I claim:

1. An apparatus for controlling gastro-pharyngeal reflux in a patient, the apparatus comprising: an enteral feeding tube having a double lumen, a gastric balloon, an esophageal balloon, a sensor for monitoring gastric pressure when enteral feeding is in process, and an external pump that regulates air or fluid pressure within said esophageal balloon, wherein the sensor monitors gastric pressure based upon a signal that is averaged using a filter algorithm, the filter algorithm configured to set that sets a gradient value that is added to actual gastric pressure, thereby defining a relative level of esophageal pressure, and wherein the pressure in the esophageal balloon is regulated by the external pump to the relative level of esophageal pressure and applied to seal from gastro-pharyngeal reflux.

2. The apparatus according to claim 1, wherein said esophageal balloon is inflatable with either a liquid or a gaseous fluid.

3. The apparatus according to claim 1, further comprising a feeding pump that senses and regulates relative amount of pressure in a patient's stomach as well as esophagus.

\* \* \* \* \*